US00PP16895P2

(12) United States Plant Patent

Hansen

(10) Patent No.: US PP16,895 P2

(45) Date of Patent: Jul. 25, 2006

(54) *HOSTA* PLANT NAMES 'JOURNEY'S END'

(50) Latin Name: ***Hosta* sp.**
Varietal Denomination: Journey's End

(75) Inventor: Hans Andrew Hansen, Waseca, MN (US)

(73) Assignee: Shady Oaks Nursery, LLC, Waseca, MN (US); (50% of Rights)

( * ) Notice: Subject to any disclaimer, the term of this patent is extended or adjusted under 35 U.S.C. 154(b) by 5 days.

(21) Appl. No.: 11/099,730

(22) Filed: Apr. 6, 2005

(51) Int. Cl.
*A01H 5/00* (2006.01)

(52) U.S. Cl. ..... Plt./353

(58) Field of Classification Search ..... Plt./353
See application file for complete search history.

*Primary Examiner*—Kent Bell
*Assistant Examiner*—June Hwu
(74) *Attorney, Agent, or Firm*—Penny J. Aguirre

(57) ABSTRACT

A new cultivar of *Hosta* named 'Journey's End', a sport of *Hosta* 'Choo Choo Train', that is characterized by its unique variegated foliage with yellow-green centers and green margins comprising about one third to one half of the leaf area. 'Journey's End' has a mounded plant habit of large broad leaves, a vigorous growth rate, and pale lavender flowers held above the foliage in early to mid summer.

2 Drawing Sheets

RELATED APPLICATIONS

This application is co-pending with U.S. Plant patent application Ser. No. 11/099,729 filed for a cultivar derived from the same parent entitled *Hosta* Plant Named 'American Icon'.

Botanical classification: *Hosta* sp.

Cultivar designation: 'Journey's End'.

BACKGROUND OF THE INVENTION

The present invention, *Hosta* 'Journey's End', relates to a new and distinct cultivar of *Hosta,* botanically known as a *Hosta* sp., hereinafter referred to as 'Journey's End'.

The inventor discovered the new cultivar, 'Journey's End', in summer of 1999 in a tissue culture lab in Waseca, Minn. 'Journey's End' originated as a naturally-occurring chimeral mutation of *Hosta* 'Choo Choo Train' (unpatented). The parent plant, *Hosta* 'Choo Choo Train', is non-variegated with yellow-green foliage. 'Journey's End' is unique in having foliage with green margins surrounding yellow-green centers. The closest comparison plant is 'American Icon' (patent pending), a sibling of 'Journey's End', which differs in having leaves with the reverse variegation pattern to 'Journey's End', yellow-green margins and green centers. 'Journey's End' can also be compared to 'Summer Serenade' (not patented), a plant of similar plant stature and leaf variegation pattern. 'Summer Serenade' is a chimeral mutation of golden foliaged 'Piedmont Gold' (not patented). 'Summer Serenade' differs form 'Journey's End' in having less ruffled leaf margins and by emerging earlier in the spring resulting in susceptibility to frost damage, particularly in the Southern portions of the U.S.

Asexual reproduction of the new cultivar was first accomplished by the inventor utilizing in vitro propagation in Waseca, Minn. in fall of 2002. Asexual reproduction of the new cultivar by division and tissue culture has shown that the unique features of 'Journey's End' are stable and reproduced true to type in successive generations.

SUMMARY OF THE INVENTION

The following traits have been repeatedly observed in trials in Iowa and Minnesota for a period of six years and represent the characteristics of the new cultivar. These attributes in combination distinguish 'Journey's End' as a new and unique cultivar of *Hosta.*

1. The foliage of 'Journey's End' is variegated with green margins and yellow-green centers, with margin width ranging from 3 to 9 cm comprising about one third to one half of the leaf area. The foliage of the parent plant, 'Choo Choo Train', is non-variegated with yellow-green foliage.
2. 'Journey's End' has large broad leaves with a mounded plant habit.
3. 'Journey's End' reaches a height of about 61 cm, exclusive of flower scapes, and a spread of about 132 cm in six years.
4. 'Journey's End' has large leaves with undulating margins when mature.
5. 'Journey's End' blooms in early to mid summer with pale lavender flowers that arise above the foliage.

BRIEF DESCRIPTION OF THE DRAWING

The accompanying colored photographs illustrate the overall appearance and distinct characteristics of the new *Hosta.* The photographs were taken in June of mature plants of 'Journey's End' and 'Choo Choo Train' as grown outdoors in Waseca, Minn. under the same conditions for six years.

Figure 1:
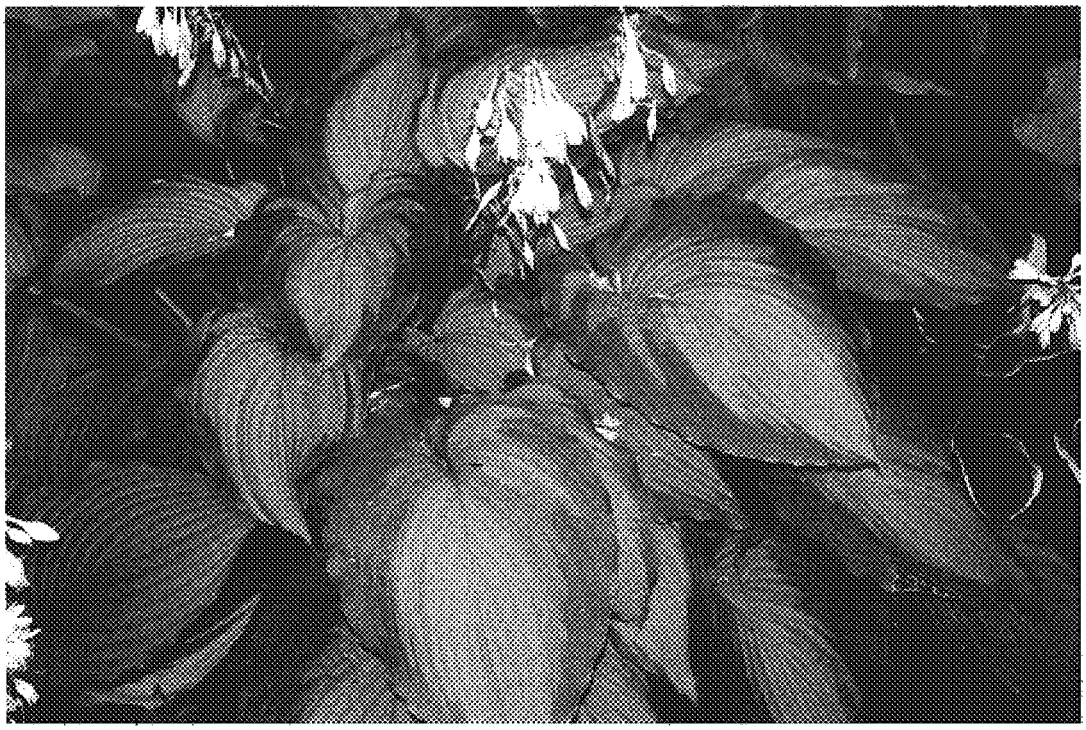
FIG. 1 provides an overall view of the foliage and plant habit of the new cultivar, 'Journey's End'.
Figure 2:
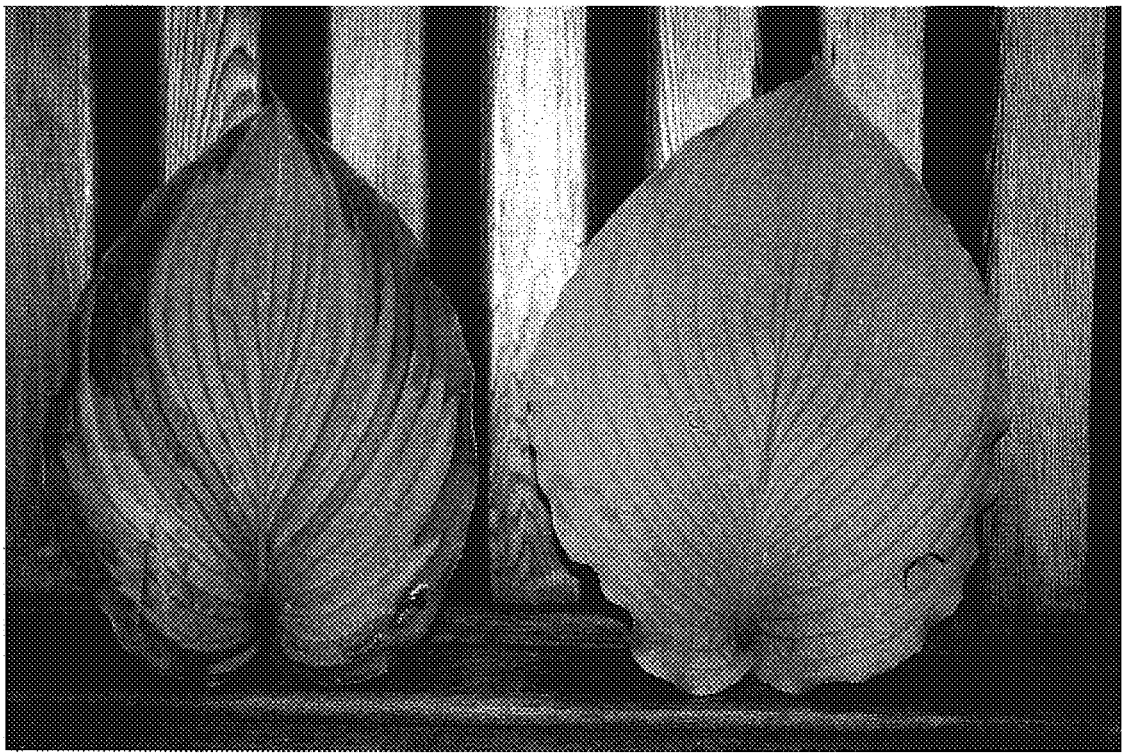

The photograph in FIG. 2 provides a comparison between a leaf of 'Journey's End' (shown on left) and 'Choo Choo Train' (shown on right) as grown in medium shade.

The colors in the photographs are as close as possible with the photographic and printing technology utilized and combined with the color values cited in the detailed botanical description accurately describe the colors of the new *Hosta*.

DETAILED BOTANICAL DESCRIPTION OF THE PLANT

The following is a detailed description of six year-old plants of the new cultivar as grown outdoors in Waseca, Minn. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

Botanical classification: 'Journey's End' is a cultivar of *Hosta* of hybrid origin.

Parentage: Naturally occurring chimeral mutation of *Hosta* 'Choo Choo Train' (not patented).

General description:

*Blooming period.*—About 4 weeks from mid June to mid July.

*Plant habit.*—Herbaceous perennial, clump-forming, mounded habit of large, broad leaves.

*Height and spread.*—Reaches about 61 cm in height (excluding flower scapes) and about 132 cm in width.

*Hardiness.*—U.S.D.A. Zones 3 to 8.

*Culture.*—Light to full shade, moist soils of moderate fertility.

*Root description.*—Freely branched, fleshy.

*Propagation.* —*In vitro* propagation is the preferred method utilizing typical methods for *Hosta,* division are also possible.

*Root development.*—Rooted transplants from tissue culture fully develop in a 96-cell liner in about 6 to 8 weeks in a greenhouse with average temperatures of about 70° F.

*Growth rate.*—Vigorous.

Foliage description:

*Leaf shape.*—Broadly ovate.

*Leaf division.*—Simple.

*Leaf base.*—Cordate.

*Leaf apex.*—Cuspidate.

*Leaf venation.*—14 pairs of veins, camptodrome pattern, impressed on upper surface and raised on lower surface, color matches leaf coloration.

*Leaf margins.*—Entire, slightly rippled on mature leaves.

*Leaf attachment.*—Petiolate.

*Leaf arrangement.*—Basal, radiate spirally from base.

*Leaf surface.*—Upper surface glabrous, lower surface slightly glaucous.

*Leaf substance.*—Average.

*Leaf orientation.*—Held horizontal on upright petioles.

*Leaf color.*—Emerging and mature foliage, upper surface; centers 144B, margins 137B, irregular intermediate area between the margins and centers 137C. The centers brighten to 11A when grown in light of high intensity, lower surface; centers 138B, margins 191A, irregular intermediate area between the margins and centers 137C.

*Leaf variegation pattern.*—Margins about 3 to 9 cm in width, comprising about one third to one half of the leaf area.

*Leaf size.*—About 37 cm in length, about 25 cm in width.

*Leaf quantity.*—About 5 to 7 per shoot (eye).

*Petiole size.*—About 56 cm in length, about 8 to 9 mm in width.

*Petiole color.*—Inner surface 144B, outer surface 137A.

*Petiole surface.*—Glabrous.

*Petiole shape.*—Sulcate.

Flower scape description:

*Scape shape.*—Round, solid.

*Scape number.*—One per mature eye under normal growing conditions.

*Scape posture.*—Straight, held upright at about 80 to 90° from horizontal.

*Scape size.*—About 80 to 86 cm in length, about 1 cm in width.

*Scape color.*—144A.

*Scape surface.*—Glabrous.

*Leaf bracts.*—None observed.

Flower description:

*Inflorescence type.*—Terminal racemes of single bell-shaped flowers on elongated scapes.

*Lastingness of inflorescence.*—About 4 weeks from first opening bloom to fading of last opening bloom, individual blooms last about one week.

*Flower shape.*—Bell-shaped.

*Flower number.*—30 to 40.

*Flower internode length.*—About 4 cm.

*Flower fragrance.*—None detected.

*Flower bud shape.*—Spathulate.

*Flower bud size.*—About 3 cm in length and 1.3 cm in diameter.

*Flower bud color.*—Emerges 92D, matures to 91D prior to opening.

*Flower size.*—About 5.5 cm in length and about 3 cm in diameter.

*Flower color.*—92D (violet-blue), slightly lighter.

*Pedicels.*—About 1 cm in length, 2 mm in diameter, 148D in color, glabrous surface.

*Perianth features.*—Comprised of 6 tepals, 3 interior and 3 exterior, overlapping in expanded region and fused in tube region.

*Tepal shape.*—Oblanceolate.

*Tepal size.*—About 5 cm in length, about 1 cm in width.

*Tepal color.*—Outer and inner surface 92D (slightly lighter), inner stripe about 1 to 2 mm in width of 76B.

*Tepal texture.*—Glabrous.

*Tepal margin.*—Entire.

*Tepal apex.*—Acute.

*Floral bracts.*—1 per flower, ovate in shape, glabrous surface, 14C in color, up to 3.5 cm in length and 1 cm in width.

Reproductive organs:

*Gynoecium.*—1 Pistil, style is about 1 cm in length, 3 mm in width and 8D in color, stigma is 3-lobed and 8D in color, ovary is superior, compound, composed of 3 locules, 146D in color.

*Androecium.*—6 stamens, filament is 8D in color, 5 cm in length, 1 mm in width, length is slightly shorter than perianth, anthers are 3 mm in length, 1 mm in width, attachment is versatile, 202A in color, dehiscence is longitudinal, pollen is abundant and 15B in color.

*Fruit*.—Capsule, 3-chambered, about 4 cm in length, 8 mm in width, 138A in color.

*Seeds*.—25 to 30 seeds per capsule, about 5 to 6 mm in length and 3 mm in width, 202A in color.

I claim:

1. A new and distinct cultivar of *Hosta* plant named 'Journey's End' as herein illustrated and described.

* * * * *